US012670556B2

(12) United States Patent
Nett et al.

(10) Patent No.: US 12,670,556 B2
(45) Date of Patent: Jun. 30, 2026

(54) REDUCING NOISE IN CT IMAGES USING SYNTHETIC DATA

(71) Applicant: GE Precision Healthcare LLC, Wauwatosa, WI (US)

(72) Inventors: Brian E. Nett, Waukesha, WI (US); Meghan L. Yue, Johnson Creek, WI (US); Nicholas Mathew, Milwaukee, WI (US); Jonathan S. Maltz, Oakland, CA (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 561 days.

(21) Appl. No.: 18/177,598

(22) Filed: Mar. 2, 2023

(65) Prior Publication Data

US 2024/0296527 A1 Sep. 5, 2024

(51) Int. Cl.
G06K 9/00 (2022.01)
A61B 6/00 (2006.01)
(Continued)

(52) U.S. Cl.
CPC .............. G06T 5/70 (2024.01); A61B 6/5247 (2013.01); A61B 6/5258 (2013.01); G06T 5/50 (2013.01); G06T 7/11 (2017.01); G06T 7/143 (2017.01); *G06T 2207/10056* (2013.01); *G06T 2207/10081* (2013.01); *G06T 2207/10088* (2013.01); *G06T 2207/10104* (2013.01); *G06T 2207/20021* (2013.01); *G06T 2207/20081* (2013.01);
(Continued)

(58) Field of Classification Search
CPC ..... G06T 5/70; G06T 5/50; G06T 7/11; G06T 7/143; G06T 2207/10056; G06T 2207/10081; G06T 2207/10088; G06T 2207/10104; G06T 2207/20021; G06T 2207/20081; G06T 2207/20084; G06T 2207/30004; G06T 5/60; A61B 6/5247; A61B 6/5258; G06N 3/04; G06N 3/08
See application file for complete search history.

(56) References Cited

U.S. PATENT DOCUMENTS 8,774,481 B2 7/2014 Schreibmann et al.
11,234,654 B2 2/2022 Han
(Continued)

OTHER PUBLICATIONS

Gholamiankhah, Faeze, Samaneh Mostafapour, and Hossein Arabi. "Deep learning-based synthetic CT generation from MR images: comparison of generative adversarial and residual neural networks." arXiv preprint arXiv:2103.01609 (2021). (Year: 2021).*
(Continued)

*Primary Examiner* — Gregory A Morse
*Assistant Examiner* — Owais I Memon
(74) *Attorney, Agent, or Firm* — McCoy Russell LLP

(57) ABSTRACT

The current disclosure provides methods and systems to reduce an amount of noise in image data. In one example, a method for creating synthetic computed tomography (CT) images for training a model to reduce an amount of noise in acquired CT images is proposed, comprising performing a tissue segmentation of reference images of an anatomical region of a subject to determine a set of different tissue types of the reference images; and generating synthetic CT images of the reference images by assigning CT image values of the synthetic CT images based on the different tissue types.

14 Claims, 10 Drawing Sheets

(51) Int. Cl.
| | |
|---|---|
| *G06T 5/50* | (2006.01) |
| *G06T 5/70* | (2024.01) |
| *G06T 7/11* | (2017.01) |
| *G06T 7/143* | (2017.01) |

(52) U.S. Cl.
CPC .............. *G06T 2207/20084* (2013.01); *G06T 2207/30004* (2013.01)

(56) References Cited

U.S. PATENT DOCUMENTS

| | | | |
|---|---|---|---|
| 2019/0209099 A1* | 7/2019 | Han ..................... | A61B 5/7267 |
| 2022/0036517 A1* | 2/2022 | Sandfort ................... | G06T 5/70 |
| 2023/0342886 A1* | 10/2023 | Meyer ...................... | G06T 5/70 |
| 2023/0342921 A1* | 10/2023 | Du ....................... | A61B 6/5211 |

OTHER PUBLICATIONS

Wolterink, J. et al., "Deep MR to CT Synthesis using Unpaired Data," ArXiv Cornell University Website, Available Online at https://arxiv.org/abs/1708.01155, Available as Early as Aug. 3, 2017, 10 pages.

* cited by examiner

660

602
604

Flair

630

602
604

T2-weighted

600

602
604

T1-weighted

REDUCING NOISE IN CT IMAGES USING SYNTHETIC DATA

TECHNICAL FIELD

Embodiments of the subject matter disclosed herein relate to medical imaging, and more particularly, to systems and methods for removing noise from computed tomography (CT) images.

BACKGROUND

Medical images such as CT images may include an amount of noise, which may reduce a quality of the images and hinder diagnosis. Various approaches have been taken to reduce or remove the noise. In some examples, a convolutional neural network (CNN) may be trained to reduce an amount the noise in the CT images. The CNN may be trained on image pairs including a first, noisy input image, and a second, noise-free target (ground truth) image. The CNN learns to map the noisy images to the noise-free images, and when trained, the CNN may output noise-reduced versions of CT images inputted into the CNN.

However, an amount of noise removed by CNNs trained in this manner may be less than desired, where the noise-reduced versions of the CT images may still include noise. One reason for this is that it may be difficult for the CNNs to distinguish noise from anatomical features of a CT image.

SUMMARY

The current disclosure includes a method for creating synthetic computed tomography (CT) images for training a model to reduce an amount of noise in acquired CT images, the method comprising performing a tissue segmentation of reference images of an anatomical region of a subject to determine a set of different tissue types of the reference images; and generating synthetic CT images of the reference images by assigning CT image values of the synthetic CT images based on the different tissue types. The model may be trained on the synthetic CT images. In various embodiments, the model is a neural network model.

The trained model may then be used to reduce noise in real CT images. The trained model may more accurately distinguish noise from the anatomical features of the synthetic CT images than real images, where a resulting performance and/or accuracy of the trained neural network model may be higher when the model is trained on the synthetic CT images than when the model is trained on real CT images. Additionally, the performance of the model may be further increased by using reference images of a higher resolution than typical CT images. For example, the reference images may be images acquired using magnetic resonance (MR) imaging, multi-energy CT imaging, spectral CT imaging, positron emission tomography (PET) imaging, single photon computed tomography (SPECT) imaging or histological images taken from anatomical samples (such as whole-slide imaging [WSI] of anatomical slices). MR reference images may be generated using pulse sequences that are optimized for the creation of high-quality synthetic CT images. Further, multi-sequence MR scanned images may be used, where a reference image may be a composite image created from a plurality of MR images, each image of the plurality of MR images generated using a different type of pulse sequence applied during a slice of a multi-sequence MR scan. In this way, noise-reduction models may be created that are more accurate than conventional models trained on real CT images.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
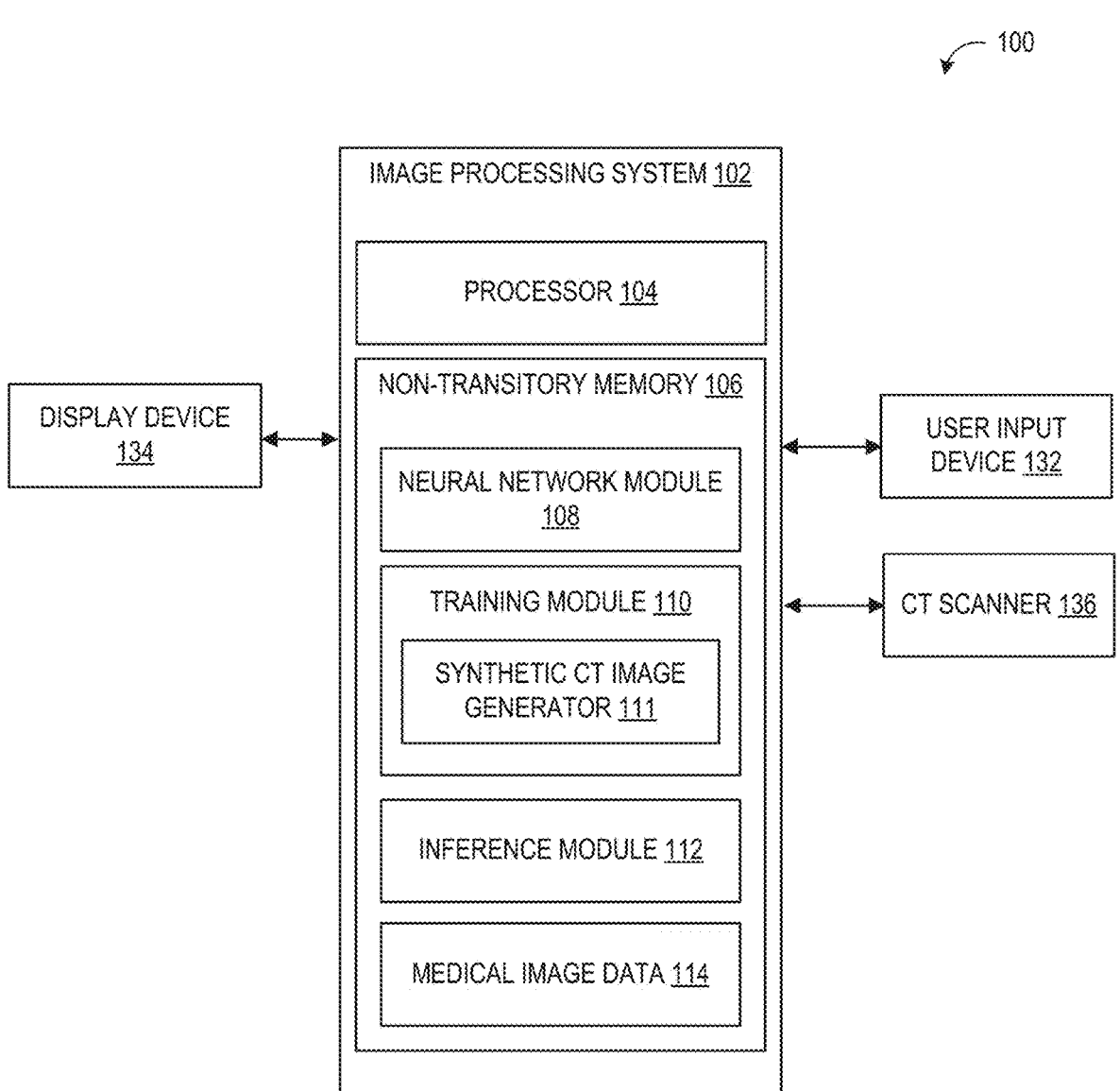
FIG. 1 shows a block diagram of an exemplary embodiment of an image processing system configured to reduce, and in some examples, remove, noise from CT images, in accordance with one or more embodiments of the present disclosure.

The drawings illustrate specific aspects of the described systems and methods. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

Methods and systems are provided herein for reducing noise in (e.g., denoising) medical image data, such as computed tomography (CT) images. Various approaches to reducing noise in CT images include using a model to map a first, noisy image to a target image including less noise. The first, noisy image may be a version of the target image with noise added. Once the model is trained, the model may be deployed to remove noise from new (e.g., unseen) CT images. In various embodiments, the model may be a neural network model, such as a convolutional neural network (CNN). However, while the model described herein is a neural network model, it should be appreciated that in other embodiments, a different type of model could be used without departing from the scope of this disclosure. For example, the model could be a different type of artificial intelligence (AI), machine learning (ML), or deep learning (DL) model, or a statistical model, or a different type of model.

However, an amount of noise removed from the CT images may be limited, where noise-reduced images outputted by the trained model still include an undesirable amount of noise. For example, differentiation of actual image detail from noise may be complicated by correlations between signal and noise. A model that learns the characteristics of actual structure and/or noise may be better able to remove noise while preserving image features (edges, texture, and contrast).

To increase a performance of such a model, a method for training a neural network model is proposed herein that relies on high quality synthetic training data. While other approaches have included training models on synthetic CT images generated from real CT images, the synthetic CT images may not be of a high enough resolution to significantly increase the performance of the models. In contrast, the methods proposed herein rely on generating synthetic CT images from a set of optimized reference images, where the optimized reference images have a higher resolution, contrast, contrast-to-noise ratio (CNR), signal-to-noise ratio (SNR) and/or other properties of the optimized reference images than CT images. Thus, a higher quality of the synthetic CT images generated from the optimized reference images may result in higher quality training data, which may lead to an increased performance of a noise reduction neural network in removing noise from CT images acquired from a patient.

In particular, the reference images may be magnetic resonance (MR) images, and optimizing the reference images may include optimizing a set of technical parameters that define pulse sequences used to generate the MR images. In other words, a set of pulse sequences may be determined that generate a highest quality (e.g., highest resolution, highest CNR, etc.) set of reference images to be used to generate the synthetic CT images. Further, MR images created with different pulse sequences may be combined to generate MR reference images with a quality higher than that of the component MR images.

Figure 6C:
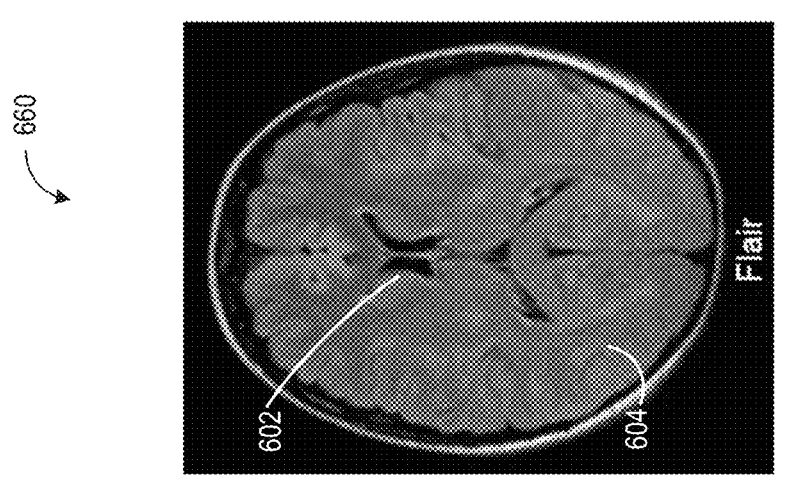
FIG. 6C shows a third example MR image generated using a third pulse sequence, in accordance with one or more embodiments of the present disclosure.
Figure 6B:
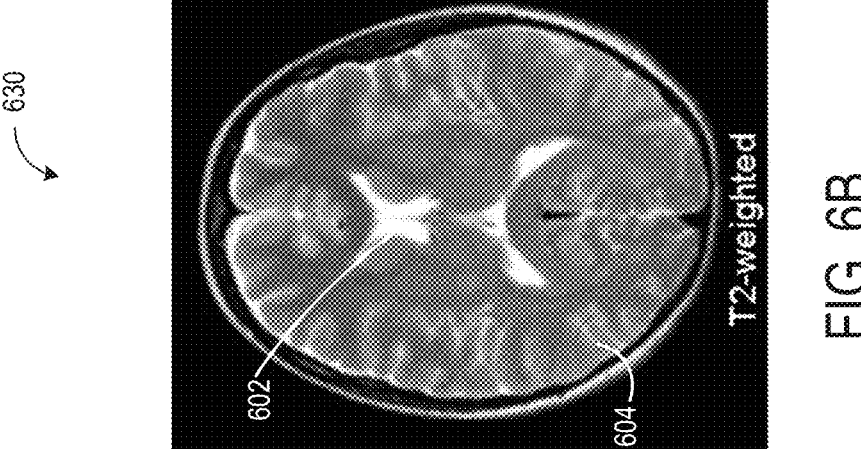
FIG. 6B shows a second example MR image generated using a second pulse sequence, in accordance with one or more embodiments of the present disclosure.
Figure 6A:
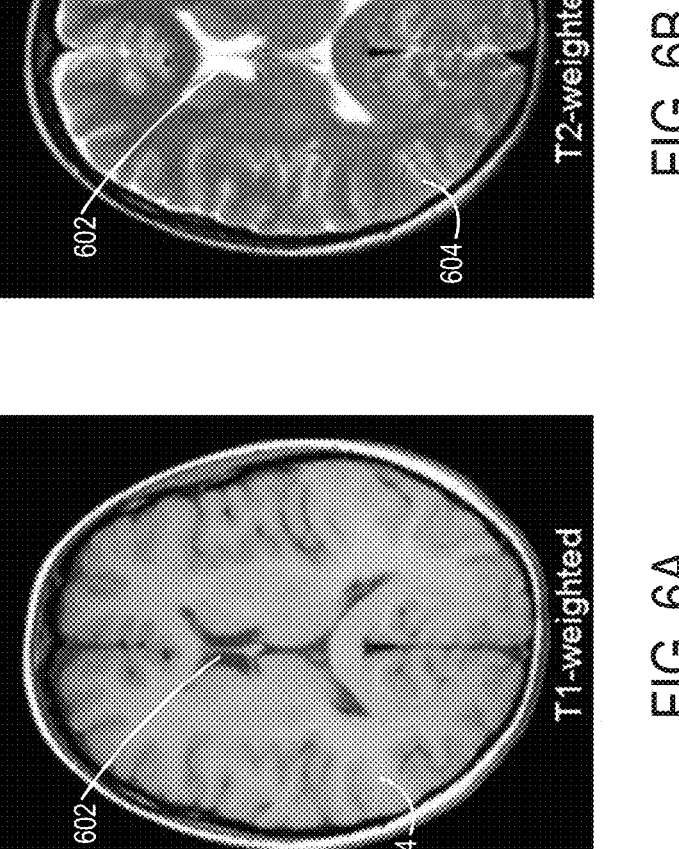
FIG. 6A shows a first example MR image generated using a first pulse sequence, in accordance with one or more embodiments of the present disclosure.
Figures 7A, 7B:
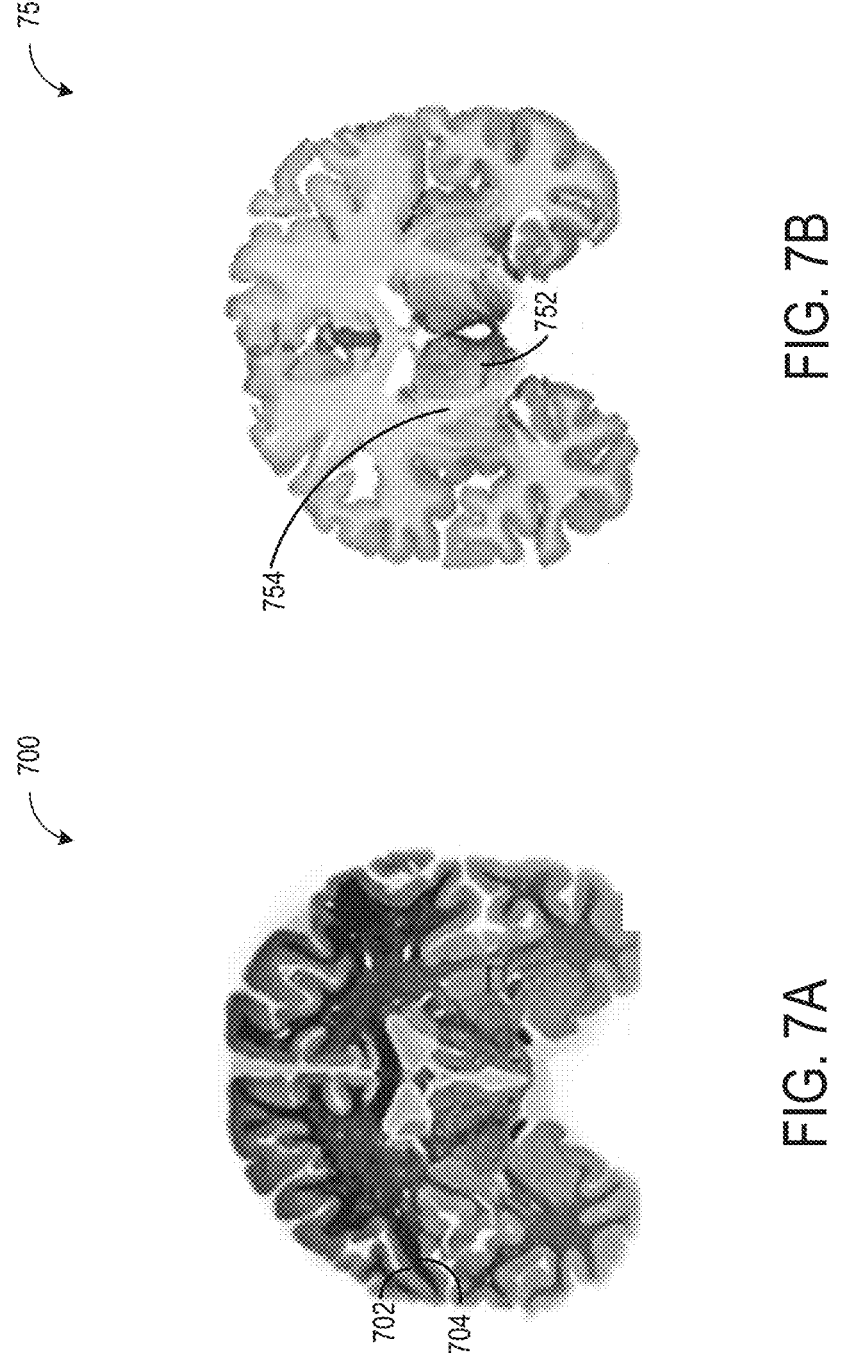
FIG. 7A shows a first example stained histology image.
FIG. 7B shows a second example stained histology image.

In an embodiment, noise may be reduced or removed from a CT image by an image processing system, such as the image processing system 102 of FIG. 1. The image processing system may include a noise reduction neural network model that takes as input a noisy CT image, and outputs a noise-reduced version of the CT image. The noise reduction neural network model may be trained by following one or more steps of the method of FIG. 3, as described in relation to the neural network training system of FIG. 2A. The noise reduction neural network model may be trained on synthetic CT data, which may be generated by following one or more steps of the method of FIG. 4, as described in relation to the training data generation system of FIG. 2B. The synthetic data may be generated from reference images including magnetic resonance (MR) images, which may be acquired using different pulse sequences, as shown in FIGS. 6A, 6B, and 6C. The reference images may also be histological images, as shown in FIGS. 7A and 7B. FIG. 9 shows an example of a synthetic CT image generated from a reference MR image. The trained noise reduction neural network model may be deployed to reduce noise in new CT images, using the method of FIG. 5. A noisy CT image shown in FIG. 8A may be inputted into the trained noise reduction neural network model, which may output a noise-reduced image shown in FIG. 8B. The noise-reduced image of FIG. 8B may be of a higher quality (e.g., may include less noise) than an image outputted by an alternative neural network model trained on real CT images, shown in FIG. 8C.

Referring to FIG. 1, an image processing system 102 of a medical imaging system 100 is shown, in accordance with an embodiment. In some embodiments, at least a portion of image processing system 102 is disposed at a device (e.g., edge device, server, etc.) communicably coupled to the medical imaging system 100 via wired and/or wireless connections. In some embodiments, at least a portion of image processing system 102 is disposed at a separate device (e.g., a workstation) which can receive images from the medical imaging system 100 or from a storage device which stores the images/data generated by the medical imaging system 100.

Image processing system 102 includes a processor 104 configured to execute machine readable instructions stored in non-transitory memory 106. Processor 104 may be single core or multi-core, and the programs executed thereon may be configured for parallel or distributed processing. In some embodiments, the processor 104 may optionally include individual components that are distributed throughout two or more devices, which may be remotely located and/or configured for coordinated processing. In some embodiments, one or more aspects of the processor 104 may be virtualized and executed by remotely-accessible networked computing devices configured in a cloud computing configuration.

Non-transitory memory 106 may store a neural network module 108, a network training module 110, an inference module 112, and medical image data 114. Neural network module 108 may include a deep learning network and instructions for implementing the deep learning network to reduce or optionally remove noise from a medical image of the medical image data 114, as described in greater detail below. Neural network module 108 may include one or more trained and/or untrained neural networks and may further include various data, or metadata pertaining to the one or more neural networks stored therein.

Training module 110 may comprise instructions for training one or more of the neural networks implementing a deep learning model stored in neural network module 108. In particular, training module 110 may include instructions that, when executed by the processor 104, cause image processing system 102 to conduct one or more of the steps of method 300 for training the one or more neural networks in a training stage, discussed in more detail below in reference to FIGS. 2A and 3. Training module 110 may include a synthetic CT image generator 111, which may be used to generate synthetic training data to train the one or more neural networks, as described in greater detail below in reference to FIGS. 2B and 4. In some embodiments, training module 110 includes instructions for implementing one or more gradient descent algorithms, applying one or more loss functions, and/or training routines, for use in adjusting parameters of the one or more neural networks of neural network module 108. Non-transitory memory 106 also stores an inference module 112 that comprises instructions for reducing an amount of noise in new image data with the trained deep learning model.

Non-transitory memory 106 further stores medical image data 114. Medical image data 114 may include for example, medical images acquired via a CT scanner, a magnetic resonance imaging (MRI) scanner, a scanner for spectral imaging, or via a different imaging modality. For example, the medical image data 114 may store images acquired via a CT scanner of the same anatomical features of a same patient. Medical image data 114 may also include histological images of anatomical structures generated from slices of anatomical specimen.

In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices configured in a cloud computing configuration.

Image processing system 102 may be operably/communicatively coupled to a user input device 132 and a display device 134. User input device 132 may comprise one or more of a touchscreen, a keyboard, a mouse, a trackpad, a motion sensing camera, or other device configured to enable a user to interact with and manipulate data within image processing system 102. Display device 134 may include one or more display devices utilizing virtually any type of technology. In some embodiments, display device 134 may comprise a computer monitor, and may display medical images. Display device 134 may be combined with processor 104, non-transitory memory 106, and/or user input device 132 in a shared enclosure, or may be peripheral display devices and may comprise a monitor, touchscreen, projector, or other display device known in the art, which may enable a user to view medical images produced by a medical imaging system, and/or interact with various data stored in non-transitory memory 106.

Image processing system 102 may be operably/communicatively coupled to a CT scanner 136. CT scanner 136 may be any CT imaging device configured to image a subject such as a patient, an inanimate object, one or more manufactured parts, and/or foreign objects such as dental implants, stents, and/or contrast agents present within the body. Image processing system 102 may receive CT images from CT scanner 136, process the received CT images via processor 104 based on instructions stored in one or more modules of non-transitory memory 106, and/or store the received CT images in medical image data 114.

It should be understood that image processing system 102 shown in FIG. 1 is for illustration, not for limitation. Another appropriate image processing system may include more, fewer, or different components.

Figure 2A:
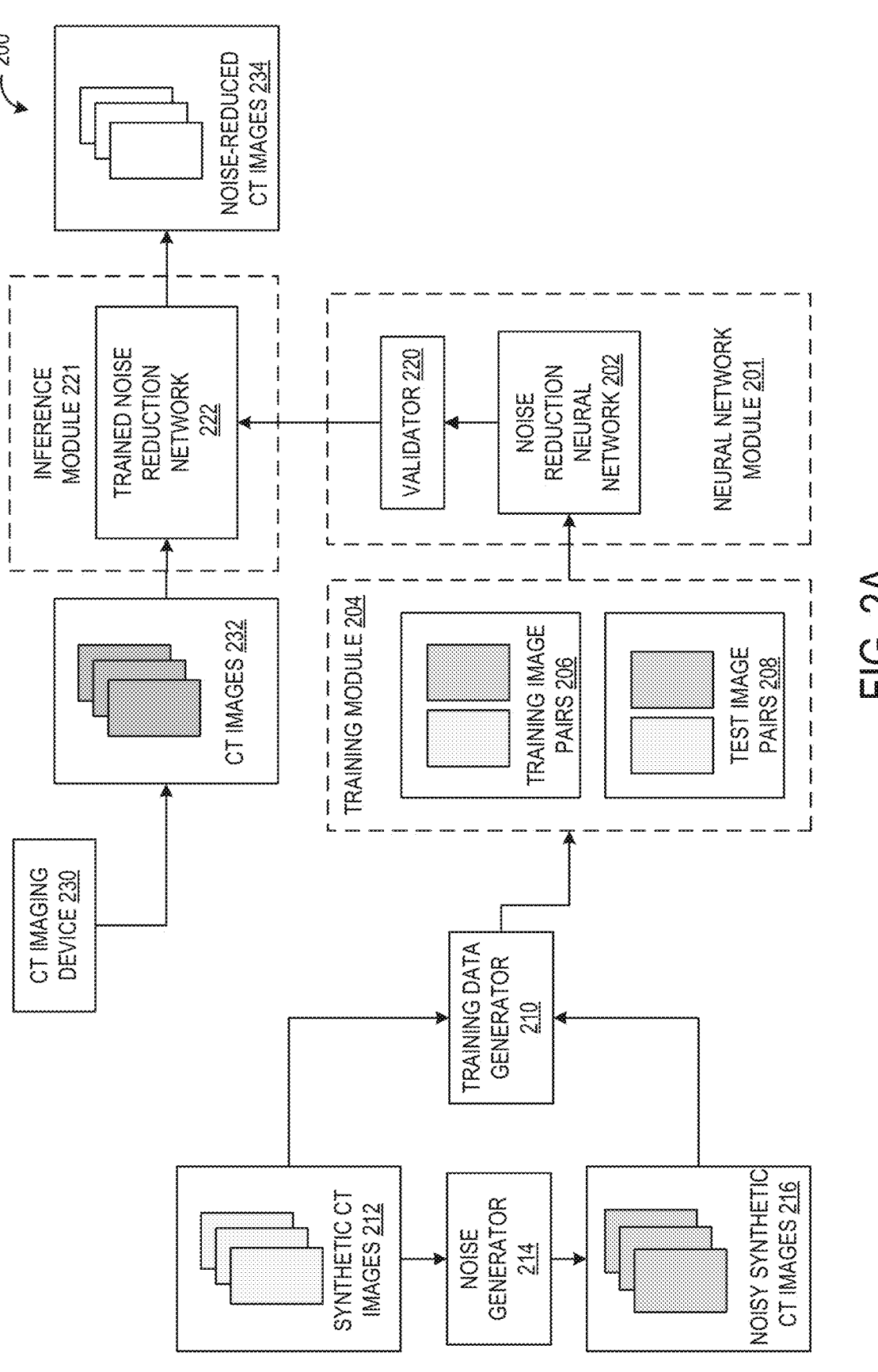
FIG. 2A shows a block diagram of an exemplary embodiment of a noise reduction neural network training system for training a neural network, in accordance with one or more embodiments of the present disclosure.

Referring to FIG. 2A, an example of a noise reduction neural network training system 200 is shown, which may be used to train a neural network such as a noise reduction neural network 202. Noise reduction neural network 202 may be trained to detect and reduce or optionally remove noise from two dimensional (2D) CT images, in accordance with one or more operations described in greater detail below in reference to method 300 of FIG. 3. Noise reduction neural network training system 200 may be implemented by an image processing system, such as image processing system 102 of FIG. 1, to train noise reduction neural network 202 to detect and reduce or optionally remove noise in a CT image.

In some embodiments, noise reduction neural network 202 may be a deep neural network with a plurality of hidden layers. In one embodiment, noise reduction neural network 202 is a convolutional neural network (CNN).

Noise reduction neural network 202 may be stored within a neural network module 201 of the image processing system. Neural network module 201 may be a non-limiting example of neural network module 108 of image processing system 102 of FIG. 1. Noise reduction neural network training system 200 also includes a training module 204, which includes a training dataset comprising a plurality of training pairs of data, such as image pairs divided into training image pairs 206 and test image pairs 208. Training module 204 may be a non-limiting example of training module 110 of image processing system 102 of FIG. 1.

A number of training image pairs 206 and test image pairs 208 may be selected to ensure that sufficient training data is available to prevent overfitting, whereby the noise reduction neural network 202 learns to map features specific to samples of the training set that are not present in the test set.

Each image pair of the training image pairs 206 and the test image pairs 208 comprises a 2D input image and a 2D target image. As described in greater detail below in reference to FIG. 2B, the input image and the target image may be synthetic CT images generated from higher resolution reference images. In various embodiments, the input image is a version of the target image with an amount of noise added to it. During training, noise reduction neural network 202 may learn to distinguish the added noise from anatomical features of the target image.

Noise reduction neural network training system 200 may include a noise generator 214, which may be used to add the noise to the synthetic CT images. The noise generator 214 may receive the synthetic CT images from a first set of synthetic CT images 212, and may add random noise to the synthetic CT images to generate a second set of noisy synthetic CT images 216. An amount of the random noise may vary across different noisy synthetic CT images 216. For example, one noisy synthetic CT images 216 may have a first amount of noise, and other noisy synthetic CT images 216 may have different amounts of noise, where the different amounts of noise may be greater amounts of noise, or lesser amounts of noise.

While in FIG. 2A noise generator 214 is depicted as adding noise to synthetic CT images 212, it should be appreciated that in some embodiments, noise may be added to projection data rather than image data. In other words, a realistic noise model may be used to add noise prior to or during image reconstruction, when a full 3D volume synthetic image is created. Adding noise is described in greater detail below in relation to FIG. 3.

Noise reduction neural network training system 200 may include a dataset generator 210, which may be used to generate the training image pairs 206 and the test image pairs 208 of the training module 204. Images from the first set of synthetic CT images 212 may be paired with images from the second set of noisy synthetic CT images 216 by dataset generator 210. An example method for generating the training data is described in further detail below with respect to FIG. 4.

Once each image pair is generated, the image pair may be assigned to either the training image pairs 206 or the test image pairs 208. In an embodiment, the image pair may be assigned to either the training image pairs 206 or the test image pairs 208 randomly in a pre-established proportion. For example, the image pair may be assigned to either the training image pairs 206 or the test image pairs 208 randomly such that 90% of the image pairs generated are assigned to the training image pairs 206, and 10% of the image pairs generated are assigned to the test image pairs 208. Alternatively, the image pair may be assigned to either the training image pairs 206 or the test image pairs 208 randomly such that 85% of the image pairs generated are assigned to the training image pairs 206, and 15% of the image pairs generated are assigned to the test image pairs 208. It should be appreciated that the examples provided herein are for illustrative purposes, and image pairs may be assigned to the training image pairs 206 dataset or the test image pairs 208 dataset via a different procedure and/or in a different proportion without departing from the scope of this disclosure.

Noise reduction neural network training system 200 may include a validator 220 that validates the performance of the noise reduction neural network 202 against the test image pairs 208. The validator 220 may take as input a partially trained noise reduction neural network 202 and a dataset of test image pairs 208, and may output an assessment of the performance of the partially trained noise reduction neural network 202 on the dataset of test image pairs 208.

Once the noise reduction neural network 202 has been validated, a trained noise reduction neural network 222 (e.g., the validated noise reduction neural network 202) may be used to generate a set of noise-reduced 2D CT images 234 from a set of acquired (e.g., real) 2D CT images 232. For example, the acquired CT images 232 may be acquired by a CT imaging device 230, which may be a non-limiting version of CT scanner 136 of FIG. 1. Trained noise reduction neural network 222 may be stored within an inference module 221 of the image processing system (e.g., inference module 112 of FIG. 1).

Figure 2B:
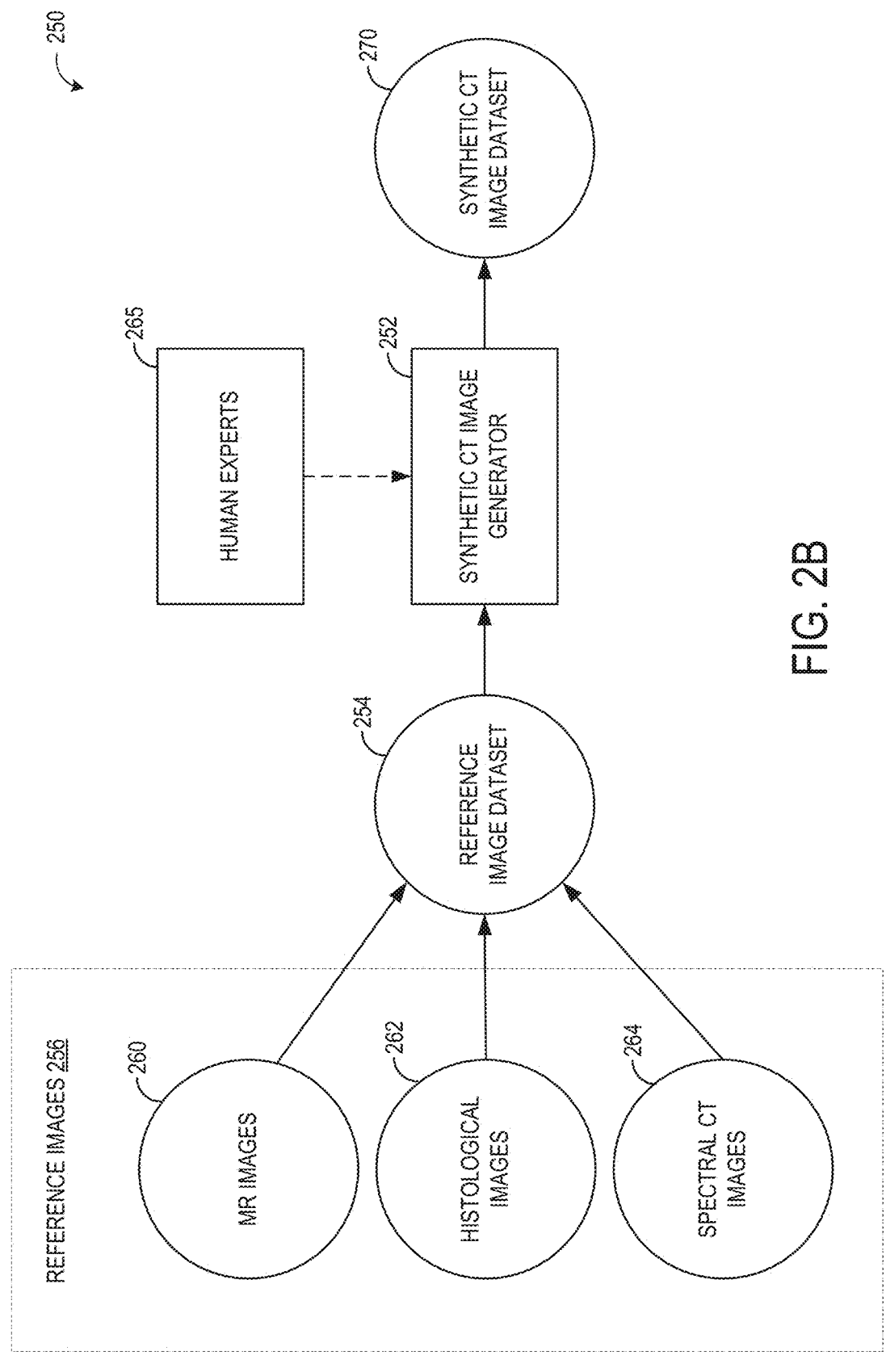
FIG. 2B shows a block diagram of an exemplary embodiment of a training data generation system for a noise reduction neural network, in accordance with one or more embodiments of the present disclosure.

FIG. 2B shows a block diagram of an exemplary embodiment of a training data generation system 250 for a noise reduction neural network, such as noise reduction neural network 202 of FIG. 2A. As described above, the noise reduction neural network may be trained on training data including CT image pairs, where the CT image pairs include synthetic input and target CT images.

Training data generation system 250 may include a synthetic CT image generator 252 (e.g., synthetic CT image generator 111 of FIG. 1) that generates the synthetic CT images. For the purposes of this disclosure, a synthetic CT image is a 2D image comprising CT image values that are assigned to regions of the image (e.g., tissues, bone, etc.) based on a segmentation of a real 3D reference image. In other words, synthetic CT image generator 252 may receive a reference image and perform a segmentation algorithm that detects and determines boundaries of different anatomical features of the reference image. The boundaries may be used to generate a set of segments to which image values may be assigned. For example, voxels included in a first segment corresponding to a first anatomical feature may be assigned a first set of image values (e.g., voxel intensity values) within a first range. Voxels of a second, adjoining segment may be assigned image values within a second range, where the second range is different from the first range. Voxels of one or more areas outside the first and second segments may be assigned image values within a third range, where the third range is different from the first range and the second range.

In some embodiments, the segmentation may be performed by synthetic CT image generator 252 in an automated fashion, without human intervention. For example, the segmentation may be performed by a segmentation module of the synthetic CT image generator, and the image values may be assigned to the resulting segments based on one or more algorithms of synthetic CT image generator 252. In some embodiments, the segmentation module may rely on a trained neural network model to perform the segmentation. The segmentation module may also rely on statistical techniques to perform the segmentation, such as thresholding or clustering algorithms (e.g., k-means clustering, nearest neighbor, etc.). In still other embodiments, the segmentation may be performed manually by one or more human experts 265, and synthetic CT image generator 252 may be used by the human experts 265 to assign the image values to the manually generated segments.

After a 3D synthetic image has been generated by segmenting the 3D reference image and assigning the voxel image values, 2D synthetic CT images may be created from the 3D synthetic image. By assigning different ranges of image values to different segments and/or areas of the reference image, a contrast between the different segments and/or areas of the 2D synthetic images may be accentuated, resulting in simplified, "cartoonized" synthetic CT images corresponding to slices of the 3D reference image. One advantage of the synthetic CT images is that a neural network such as the noise reduction neural network may more easily distinguish different anatomical features of the simplified, synthetic CT image than features of a real CT image.

Synthetic CT image generator 252 may receive reference images from a reference image dataset 254. Reference image dataset 254 may include a plurality of reference images 256, which may come from various sources and/or include various types of images. For example, reference images 256 may include a first plurality of MR images 260; a second plurality of histological images 262; and a third plurality of spectral CT images 264. The first, second, and third pluralities may include different numbers of images, or the same number of images, or no images. For example, in one embodiment, reference images 256 may include MR images 260 and may not include histological images 262 and spectral CT images 264; in another embodiment, reference images 256 may include histological images 262 and may not include MR images 260 and spectral CT images 264; in yet another embodiment, reference images 256 may include histological images 262 and MR images 260 and may not include spectral CT images 264; and so on. Use of multiple reference images is generally preferred so as to better generate synthetic CT images, based on the incremental independent information that may be contributed by each reference image. It should be appreciated that the examples of reference images described herein are for illustrative purposes, and additional and/or different types of images may be included in reference images 256 without departing from the scope of this disclosure. For example, reference images 256 may include CT images from a multi-energy CT imaging device, or a different CT imaging device, positron emission tomography (PET) images, and/or other types of images acquired via other types of imaging devices. A single imaging method may contribute more than one reference image. For example: histological images may be obtained with different stains and/or different illumination spectrum; PET images may be obtained using more than one injected/applied/inhaled tracer agent.

The different types of images included in reference images 256 may include image types with a higher quality than typical CT images. For example, histological images and MR images may have a higher resolution, less noise, and/or an increased soft-tissue contrast with respect to a CT image of a same subject. By leveraging spectral information, the spectral CT images may include more image data than a CT image. By generating the synthetic CT images from the higher-quality reference images 256 rather than from real CT images, the resulting synthetic CT images may have higher resolution, less noise, and/or an increased soft-tissue contrast than synthetic CT images generated from the real CT images. Additionally, reference images 256 may be optimized for creating high resolution synthetic CT images. For example, MR images may be optimized based on one or more pulse sequences used in image acquisition, and MR images may be combined to form composite MR images with desired characteristics. A first set of MR images may be created, from which a second set of MR images may be selected, where the MR images of the second set have a resolution above a threshold resolution. Optimization of reference images is described in greater detail below in reference to FIG. 3.

Once reference images 256 have been generated, optimized, and/or selected, they may be added to reference image dataset 254 to be processed by synthetic CT image generator 252. Synthetic CT image generator 252 may generate 2D synthetic CT images from the selected reference images, which may be stored in a synthetic CT image dataset 270. Synthetic CT image dataset 270 may be used to generate training and test image pairs as described above in reference to FIG. 2A. For example, synthetic CT images 212 of FIG. 2A may be drawn from synthetic CT image dataset 270 by noise generator 214 to generate the noisy synthetic CT images 216, and/or by dataset generator 210 to create training image pairs 206 and test image pairs 208.

Figure 3:
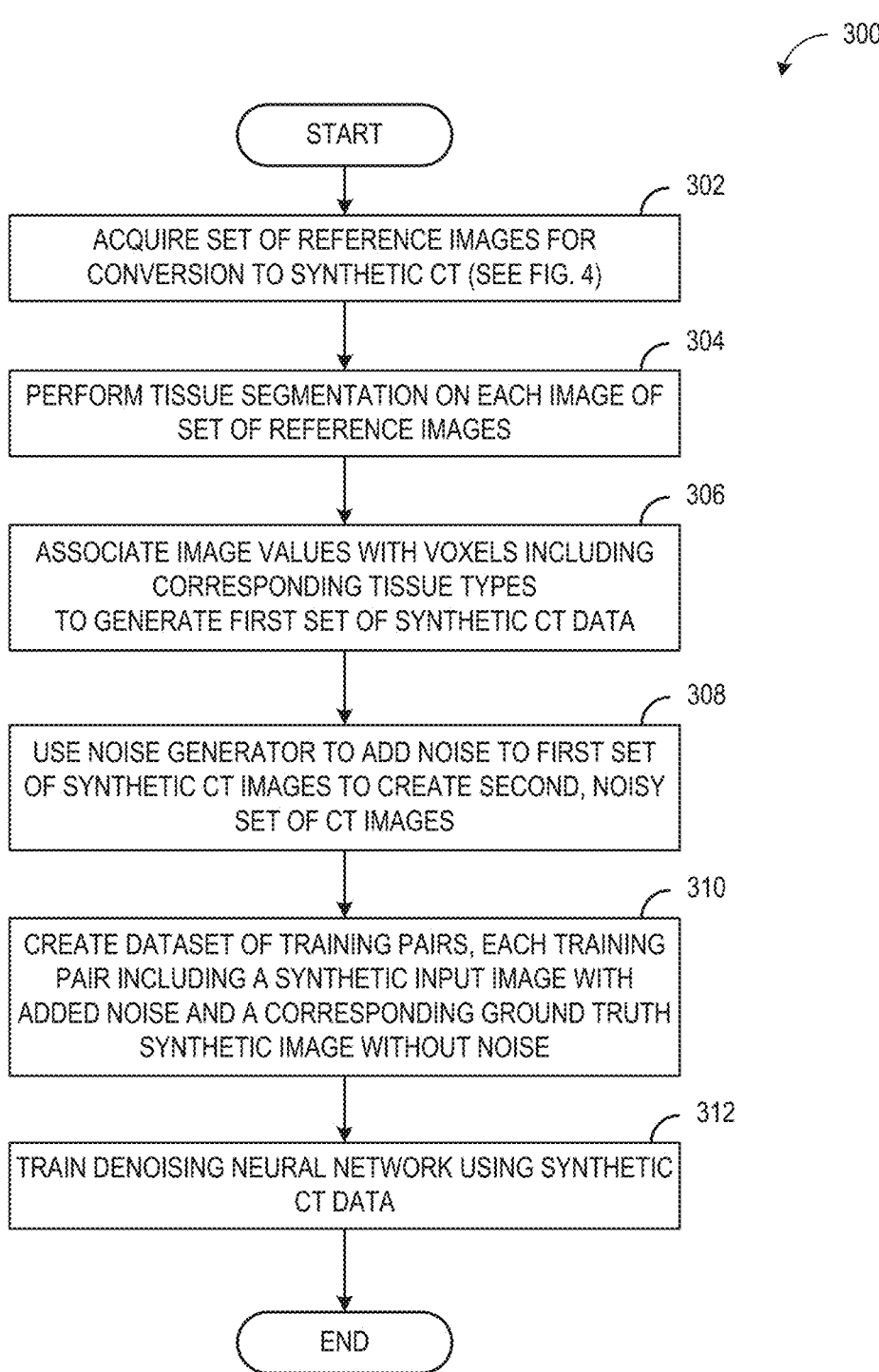
FIG. 3 shows a flowchart illustrating an exemplary method for training a noise reduction neural network, in accordance with one or more embodiments of the present disclosure.

Referring now to FIG. 3, a flowchart is shown of a method 300 for training a noise reduction neural network. The noise reduction neural network may be a non-limiting example of the noise reduction neural network 202 of the noise reduction neural network training system 200 of FIG. 2A, according to an exemplary embodiment. Method 300 may be executed by a processor of an image processing system, such as the image processing system 102 of FIG. 1. In an embodiment, some operations of method 300 may be stored in non-transitory memory of the image processing system (e.g., in a training module such as the training module 110 of the image processing system 102 of FIG. 1) and executed by a processor of the image processing system (e.g., the processor 104 of image processing system 102 of FIG. 1). The noise reduction neural network may be trained on training data comprising one or more sets of image pairs. Each image pair of the one or more sets of image pairs may comprise synthetic CT images with different amounts of noise, as described below. In some embodiments, the one or more sets of image pairs may be stored in a medical image dataset of an image processing system, such as the medical image data 114 of image processing system 102 of FIG. 1.

Method 300 begins at 302, where method 300 includes acquiring a set of 3D reference images that may be used to generate a set of 2D synthetic CT images. The reference images may be a non-limiting example of reference images 256 of FIG. 2B, and may include various types of images with a higher resolution than CT images (e.g., MR images, histological images, spectral CT images, etc.). The reference images may have a low level of noise. For example, spectral CT images may be acquired via a high-dose PCCT scan of a subject (e.g., 100 mA), or the histological images may be created by taking a high-resolution scan of tissue samples. Acquiring the reference images is described in greater detail below in reference to FIG. 4.

At 304, method 300 includes performing a tissue segmentation process on each image volume of the set of reference images. In some embodiments, the tissue segmentation process may be an automated segmentation process performed by a synthetic CT image generator, such as synthetic CT image generator 252 of FIG. 2B. For example, automated segmentation may be performed using one or more statistical techniques, such as thresholding or clustering methods. Alternatively, the automated segmentation may be performed by one or more AI models, such as a neural network model trained to segment tissues in medical images. In other embodiments, the tissue segmentation process may be performed manually by human experts (e.g., human experts 265). As a result of the tissue segmentation process, boundaries of anatomical features in the reference images may be detected, where certain segments (e.g., bounded regions) of the reference images may be associated with the anatomical features.

At 306, method 300 includes associating different image values (e.g., representations of signals) to voxels including corresponding tissue types, to generate a first set of synthetic CT data. In various embodiments, the image values may be voxel intensity values between 0.0 and 1.0, where an image value of 1.0 corresponds to a brightest (e.g., white) voxel, and an image value of 0.0 corresponds to a darkest (e.g., black) voxel. Image values between 0.0 and 1.0 may generate lighter and darker shades of the reference image. The lighter and darker shades of the reference image may correspond to lighter or darker tissues in a real CT image acquired of a same scanned region of interest, and/or lighter or darker tissues of a synthetic CT image generated from the reference image.

In other words, a first set of voxels included in a first segment of a reference image may be assigned image values corresponding to a first tissue type; a second set of voxels included in a second segment of the reference image may be assigned image values corresponding to a second tissue type; a third set of voxels included in a third segment of the reference image may be assigned image values corresponding to a third tissue type; and so on. For example, the first segment may be associated with bone tissues, and the first segment may be assigned higher image values (e.g., close to 1.0) such that the bone tissues are represented in a synthetic CT image as a bright region. The second segment may be associated with a first set of soft tissues, and the second segment may be assigned lower image values (e.g., between 0.0 and 1.0), such that the first set of soft tissues are represented in a synthetic CT image as a less bright region than the bone. The third segment may be associated with a second set of soft tissues, and the third segment may be assigned even lower image values (e.g., close to 0.0), such that the third set of soft tissues are represented in a synthetic CT image as a darker region than the bone and the first set of soft tissues. In the synthetic CT image, a contrast between the first, second, and third regions may highlight boundaries of the first, second, and third regions, where voxel intensity values within each region may be the same or similar, and voxel intensity values between the regions may be greater than a threshold value. As a result, it may be easier for the noise reduction neural network to distinguish between the segmented regions in the synthetic CT image than corresponding regions in the reference image.

Once 3D synthetic CT image volumes have been created from the reference images, the synthetic CT image generator may generate the first set of 2D synthetic CT images to be used to train the noise reduction neural network from the 3D synthetic CT image volumes.

FIG. 9 shows a synthetic image generation diagram 900 including an example synthetic 2D CT image 906 generated from a 2D reference image 902. In synthetic image generation diagram 900, reference image 902 is an example of real high-resolution data captured by an MR scanner. (e.g., an MR image 260 of FIG. 2B). In other embodiments, reference image 902 may be different type of image, such as a histological image or a spectral CT image (e.g., histological images 262 or spectral CT images 264, respectively). A segmentation image 904 may be generated from reference image 902, where segmentation image 904 is a segmentation of reference image 902 based on several classes of tissue type. Put another way, every pixel in reference image 902 that represents white matter is assigned a value of '1' in segmentation image 904. Synthetic CT image 906 may be generated from reference image 902 by a synthetic CT image generator, such as synthetic CT image generator 252 of FIG. 2B. Synthetic CT image 906 may be the same as segmentation image 904, but with the pixel values being assigned realistic Hounsfield (CT) units, relative to what tissue type they represent. For example, every pixel in segmentation image 904 that represents white matter has a 1, but in synthetic CT image 906, those pixels are assigned to values that correspond to white matter on the Hounsfield scale (e.g. 25). The Hounsfield scale is a standardized scale used in CT imaging and is related to the x-ray attenuation coefficient of materials.

Returning to method 300, at 308, method 300 includes using a noise generator (e.g., noise generator 214 of FIG. 2A) to add noise to the first set of synthetic CT images. The noise generator may include or be based on a realistic noise model that generates noise similar to naturally occurring noise in CT images. For example, the realistic noise model may use image-based noise insertion, where noise is added to image data, or projection-based noise insertion, where noise is added to projection data prior to image reconstruction, or a combination of image-based noise insertion and projection-based noise insertion.

For example, the noise generator may take a synthetic CT image as input, and output a version of the synthetic CT image with an added amount of noise. The added amount of noise may be a random amount of noise. For example, noise may be added to a synthetic CT image in a Gaussian distribution around a randomly selected amount of noise. For example, in one embodiment, a first randomly selected amount of noise may correspond to a low-dose CT scan with a milliampere setting of 75 mA. For a subsequent synthetic CT image inputted into the noise generator, noise may be added in a Gaussian distribution around a different randomly selected amount of noise. In other embodiments, a different distribution may be used, such as a uniform distribution.

For each image of the first set of synthetic CT images, a corresponding noise-added synthetic CT image may be created. The noise-added synthetic CT images may be the same as noisy synthetic CT images 216 of FIG. 2A.

At 310, method 300 includes generating a dataset of training pairs of synthetic CT images, where each training pair includes a target synthetic CT image with low or no noise, and a corresponding version of the synthetic CT image with added noise as an input image. In an embodiment, the input image and the target image may be paired by a dataset generator, such as the dataset generator 210 of the noise reduction neural network training system 200 of FIG. 2A. Once the image pairs have been created, the image pairs may be divided into training image pairs and test image pairs, as described above in reference to FIG. 2A.

At 312, method 300 includes training the noise reduction neural network on the training pairs. More specifically, training the noise reduction neural network on the image pairs includes training the noise reduction neural network to learn to map the higher-noise images (e.g., the synthetic CT images with added noise) to the lower-noise images. In some embodiments, the noise reduction neural network may comprise a generative neural network. In some embodiments, the noise reduction neural network may comprise a generative neural network having a U-net architecture. In some embodiments, the noise reduction neural network may include one or more convolutional layers, which in turn comprise one or more convolutional filters (e.g., a convoluted neural network architecture). The convolutional filters may comprise a plurality of weights, wherein the values of the weights are learned during a training procedure. The convolutional filters may correspond to one or more visual features/patterns, thereby enabling the noise reduction neural network to identify and extract features from the medical images. In other embodiments, the noise reduction neural network may not be a convolutional neural network, and may be a different type of neural network.

Training the noise reduction neural network on the image pairs may include iteratively inputting an input image of each training image pair into an input layer of the noise reduction neural network. In some embodiments, each pixel intensity value of the input image may input into a distinct neuron of the input layer of the noise reduction neural network. The noise reduction neural network may map the input image to a corresponding target image by propagating the input image from the input layer, through one or more hidden layers, until reaching an output layer of the noise reduction neural network. In some embodiments, the output of the noise reduction neural network comprises a 2D matrix of values, wherein each value corresponds to a distinct intensity of a pixel of the input image, and wherein a distinct intensity of each pixel of the output image generates a reconstruction of the input image where an amount of noise in one or more regions of the output image is lower than an amount of noise in the one or more regions of the input image.

The noise reduction neural network may be configured to iteratively adjust one or more of the plurality of weights of the noise reduction neural network in order to minimize a loss function, based on an assessment of differences between the input image and the target image comprised by each image pair of the training image pairs. In one embodiment, the loss function is a Mean Absolute Error (MAE) loss function, where differences between the input image and the target image are compared on a pixel-by-pixel basis and summed. In another embodiment, the loss function may be a Structural Similarity Index (SSIM) loss function. In other embodiments, the loss function may be a minimax loss function, or a Wasserstein loss function. It should be appreciated that the examples provided herein are for illustrative purposes, and other types of loss functions may be used without departing from the scope of this disclosure.

The weights and biases of the noise reduction neural network may be adjusted based on a difference between the output image and the target (e.g., ground truth) image of the relevant image pair. The difference (or loss), as determined by the loss function, may be backpropagated through the neural learning network to update the weights (and biases) of the convolutional layers. In some embodiments, back propagation of the loss may occur according to a gradient descent algorithm, wherein a gradient of the loss function (a first derivative, or approximation of the first derivative) is determined for each weight and bias of the deep neural network. Each weight (and bias) of the noise reduction neural network is then updated by adding the negative of the product of the gradient determined (or approximated) for the weight (or bias) with a predetermined step size. Updating of the weights and biases may be repeated until the weights and biases of the noise reduction neural network converge, or the rate of change of the weights and/or biases of the deep neural network for each iteration of weight adjustment are under a threshold.

In order to avoid overfitting, training of the noise reduction neural network may be periodically interrupted to validate a performance of the noise reduction neural network on the test image pairs. In an embodiment, training of the noise reduction neural network may end when a performance of the noise reduction neural network on the test image pairs converges (e.g., when an error rate on the test set converges on or to within a threshold of a minimum value). In this way, the noise reduction neural network may be trained to generate a reconstruction of an input image, where the reconstruction of the input image includes less noise than the input image.

In some embodiments, an assessment of the performance of the noise reduction neural network may include a combination of a minimum error rate and a quality assessment, or a different function of the minimum error rates achieved on each image pair of the test image pairs and/or one or more quality assessments, or another factor for assessing the performance of the noise reduction neural network. It should be appreciated that the examples provided herein are for illustrative purposes, and other loss functions, error rates, quality assessments, or performance assessments may be included without departing from the scope of this disclosure.

Figure 4:
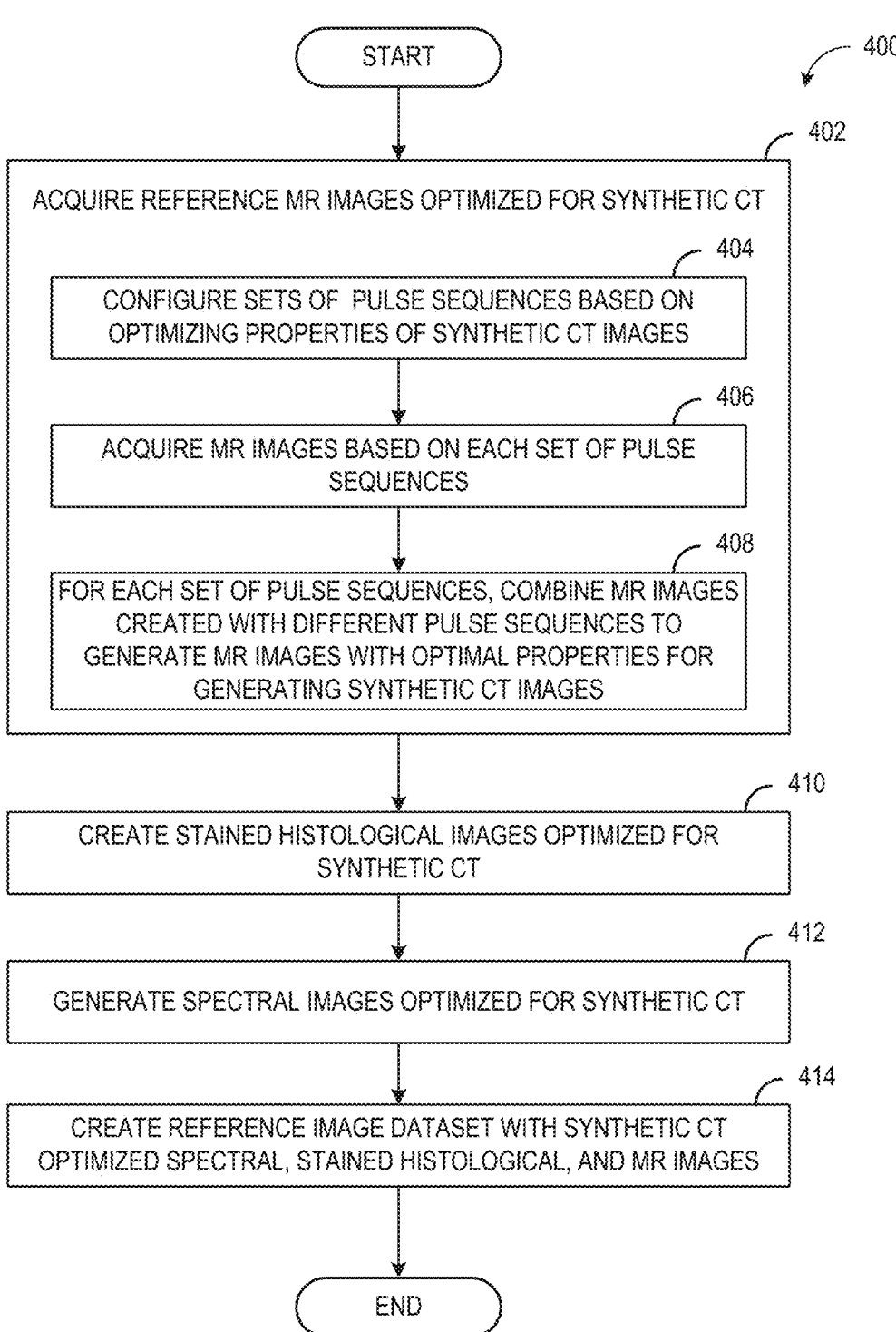
FIG. 4 shows a flowchart illustrating an exemplary method for generating training data to train a noise reduction neural network, in accordance with one or more embodiments of the present disclosure.

Referring now to FIG. 4, a flowchart is shown of a method 400 for generating training data to train a noise reduction neural network, such as noise reduction neural network 202 of noise reduction neural network training system 200 of FIG. 2A. The training data may comprise reference images of various types, where the reference images have a greater resolution and/or CNR than CT images. Some portions of method 400 may be executed by a processor of an image processing system, such as the image processing system 102 of FIG. 1. In an embodiment, some operations of method 300 may be stored in non-transitory memory of the image processing system (e.g., in a training module such as the training module 110 of the image processing system 102 of FIG. 1) and executed by a processor of the image processing system (e.g., the processor 104 of image processing system 102 of FIG. 1). Other portions of method 400 may be performed manually. Manual portions of method 400 may be performed using components of the image processing system and/or the noise reduction neural network training system.

Method 400 begins at 402, where method 400 includes acquiring a set of reference MR images that are optimized for generating synthetic CT images. At 404, acquiring the set of optimized MR images includes configuring sets of pulse sequences based on optimizing properties of synthetic CT images.

Anatomical features of a subject may be imaged using one or more pulse sequences during each slice. Each pulse sequence may generate an MR image with different characteristics. For example, a first pulse sequence may generate a first MR image with a first contrast-to-noise ratio (CNR) for a first set of soft tissues, and a second MR image with a second CNR for a second set of bone tissues, where the first CNR is higher than the second CNR. A second, different pulse sequence may generate a third MR image with a third CNR for the first set of soft tissues, and a fourth CNR for the second set of bone tissues, where the fourth CNR is higher than the second CNR. Thus, if a noise reduction neural network is trained on synthetic CT images of primarily soft tissues, training MR images may be generated using the first pulse sequence. If the noise reduction neural network is trained on synthetic CT images of primarily bone tissues, the training MR images may be generated using the second pulse sequence. If the noise reduction neural network is trained on synthetic CT images of a variety of tissues including soft tissues and harder (e.g., bone) tissues, the training MR images may include a first portion of images generated using the first pulse sequence, and a second portion of images the second pulse sequence.

Optimizing MR images for generating synthetic CT images may include identifying, out of a set of potential pulse sequences, one or more pulse sequences that enable or optimize a segmentation of a given type of tissue. For example, a first pulse sequence may be optimized for segmentation of bone tissues in an MR image of a brain; a second pulse sequence may be optimized for segmentation of white matter in the MR image of the brain; and a third pulse sequence may be optimized for segmentation of gray matter in the MR image of the brain. Each pulse sequence may be defined by a plurality of technical parameters. Determining the one or more pulse sequences that enable or optimize a segmentation of a given type of tissue may include selecting one or more sets of technical parameters that increase a desired characteristic of a synthetic CT image, such as resolution, CNR, etc. For example, the technical parameters may include a slice thickness defined by the pulse sequence; an effective T1 weighting (pulse echo sequence weighted by spin-lattice nuclear relaxation) defined by the pulse sequence; an effective T2 weighting (pulse echo sequence weighted by spin-spin nuclear relaxation) defined by the pulse sequence; an effective T2*weighting defined by the pulse sequence, where T2*relaxation refers to the decay of transverse magnetization caused by a combination of spin-spin relaxation and magnetic field inhomogeneity, which is a main source of contrast in gradient-echo magnetic resonance imaging; a proton-density weighting defined by the pulse sequence; a fat nulling defined by the pulse sequence; and a diffusion weighting defined by the pulse sequence, among others.

In some embodiments, the sets of technical parameters generating pulse sequences that enable or optimize the segmentation of the given type of tissue may be determined manually by a process of trial and error. In other embodiments, the pulse sequences may be determined by following an algorithmic procedure. A starting set of technical parameters may be selected, and the algorithmic procedure may specify how the technical parameters are adjusted over various iterations of pulse sequences generated by the adjusted technical parameters. Images reconstructed from the pulse sequences may then be compared, via a manual or automated process, to determine combinations of technical parameters used to generate images with a highest resolution. The combinations of the technical parameters may then be used to define the set of pulse sequences that enable or optimize the segmentation of the given type of tissue.

At 406, acquiring the set of optimized MR images includes acquiring a plurality of MR images based on each set of pulse sequences.

At 408, acquiring the set of optimized MR images includes, for each set of pulse sequences, optionally combining the MR images created with the different pulse sequences to generate combined or composite MR images with a highest resolution for generating synthetic CT images. For example, in the example provided above, if the noise reduction neural network is trained on synthetic CT images of the variety of tissues including soft tissues and harder (e.g., bone) tissues, the training MR images may include composite images, where the composite images may be a combination of a first image generated using the first pulse sequence, and a second image generated using the second pulse sequence.

When two or more MR images acquired using different pulse sequences are combined, a resulting combined image may reflect a weighting of each component MR image of the combined image. For example, a first combined image may have a first relative weighting of a first plurality of component images, where the component images contribute image data to the combined image in proportion to a first set of relative weights assigned to the component images. A second combined image may have a second relative weighting of a second plurality of component images, where the component images contribute image data to the combined image in proportion to a second set of relative weights assigned to the component images. In this way, MR images with a desired set of characteristics (e.g., a desired CNR, resolution, etc.) may be generated by combining MR images with different pulse sequences in accordance with different relative weightings.

Turning briefly to FIGS. 6A, 6B, and 6C, 2D MR images taken from a 3D MR reference image acquired with different pulse sequences are shown. FIG. 6A shows a first MR image 600 of a brain of a subject acquired with a first pulse sequence. First MR image 600 may have a first CNR and a first resolution. First MR image 600 includes a first anatomical structure 602 and a second anatomical structure 604. For example, first anatomical structure 602 may comprise bone tissue, and second anatomical structure 604 may comprise soft brain tissue. As a result of first MR image 600 being acquired with the first pulse sequence, a first set of voxel intensity values may be assigned to first anatomical structure 602 and second anatomical structure 604.

FIG. 6B shows a second MR image 630 of the brain of the subject acquired with a second pulse sequence. Second MR image 630 may have a second CNR and a second resolution, where the second CNR and second resolution are different from the first CNR and first resolution, respectively. Second MR image 630 includes first anatomical structure 602 and a second anatomical structure 604. As a result of second MR image 630 being acquired with the second pulse sequence, a second set of voxel intensity values may be assigned to first anatomical structure 602 and second anatomical structure 604.

FIG. 6C shows a third MR image 660 of the brain of the subject acquired with a third pulse sequence. Third MR image 660 may have a third CNR and a third resolution, where the third CNR and third resolution are different from the first and second CNRs and first and second resolutions, respectively. As a result of third MR image 660 being acquired with the third pulse sequence, a third set of voxel intensity values may be assigned to first anatomical structure 602 and second anatomical structure 604.

The voxel intensity values assigned to first MR image 600, second MR image 630, and third MR image 660 may differentially highlight first anatomical structure 602 and second anatomical structure 604. For example, third MR image 660 may show the harder tissues of first anatomical structure 602 with a higher (e.g., desirable) contrast and resolution, but may show the softer tissues of second anatomical structure 604 with a lower (e.g. undesirable) contrast and resolution. Alternatively, second MR image 630 may show the softer tissues of second anatomical structure 604 with a higher contrast and resolution, and may show the harder tissues of first anatomical structure 602 with a lower contrast and resolution. Second MR image 630 may show a higher contrast between gray tissues of the brain and white tissues of the brain than first MR image 600. As a result, a first set of MR images acquired with the second pulse sequence may be selected as reference images for training a first noise reduction neural network to remove noise from images including soft tissues, and a second set of MR images acquired with the third pulse sequence may be selected as reference images for training a second noise reduction neural network to remove noise from images including harder tissues. Alternatively, second MR image 630 and third MR image 660 (and/or first MR image 600) may be combined to generate a combined MR image having a desirable CNR and resolution in areas of the combined MR image including both harder and softer tissues. For example, second MR image 630 and third MR image 660 (and/or first MR image 600) may be inputted into a CT image synthesis engine, and the CT image synthesis engine may output a synthetic CT image based on the inputted images. Various parameters of the CT image synthesis engine may be set by an operator of the CT image synthesis engine, to generate a synthetic CT image with desired characteristics.

For example, a synthetic head CT may be generated using a combination of two or more of:

1. A CT image in which bone is most clearly represented by higher intensity regions;
2. A T2-weighted (pulse echo sequence weighted by spin-spin nuclear relaxation) MR image to clearly represent cerebrospinal fluid (CSF) and regions containing fluid as high intensity regions; and
3. A T1-weighted (pulse echo sequence weighted by spin-lattice nuclear relaxation) to best differentiate gray and white brain matter.

MR images may be combined in 3D space or in 2D space. When 2D second MR image 630 and 2D third MR image 660 are combined, pixel intensity values of the resulting combined MR image may be generated as a function of corresponding pixel intensity values of second MR image 630 and third MR image 660, where the function takes into consideration a relative weighting of second MR image 630 and third MR image 660. In some embodiments, a same function and same relative weighting may be used for all the pixel intensity values of the combined MR image. In other embodiments, different functions and/or different relative weightings may be used for different portions of the combined MR image. For example, a first set of pixel intensity values of the combined MR image corresponding to an area of first anatomical structure 602 may be generated as a first function of corresponding pixel intensity values of second MR image 630 and third MR image 660. A second set of pixel intensity values of the combined MR image corresponding to an area of second anatomical structure 604 may be generated as a second function of corresponding pixel intensity values of second MR image 630 and third MR image 660. In this way, the combined MR image may include desired characteristics of both second MR image 630 and third MR image 660 (and/or desired characteristics of first MR image 600). In other embodiments, 3D MR reference images may be combined by following a similar voxel-based procedure.

In order not to rely on a registration of scan slices to ensure that anatomical structures 602 and 604 are located at a same location within each of first MR image 600, second MR image 630, and third MR image 660, rather than following a standard imaging procedure where a full volume may be acquired, for example, slice by slice for each pulse sequence; image acquisitions with different pulse sequences may be performed during each slice. For example, in a first slice of the full volume, first MR image 600 may be acquired using the first pulse sequence; second MR image 630 may be acquired using the second pulse sequence, and third MR image 660 may be acquired using the third pulse sequence. For a second, subsequent slice, a fourth MR image may be acquired using the first pulse sequence; a fifth MR image may be acquired using the second pulse sequence, and a sixth MR image may be acquired using the third pulse sequence. In this way, the full volume may not be imaged multiple times, which may lead to images acquired with different pulse sequences having misaligned anatomical features.

Returning to FIG. 4, at 410, method 400 includes creating a plurality of stained histological images optimized for generating synthetic CT images. The histological images (e.g., histological images 262 of FIG. 2B) may be obtained from high-resolution scans of slices of tissue samples. For example, ex vivo brain slices may be obtained using an instrument such as a microtome. A staining material may be applied to the slice. The slice may be imaged, using, for example visible light. The slice may be scanned by a light source such as a laser at one or more wavelengths in order to provide either monochrome, chromatic or hyperspectral images. A slide may contain, for example, information pertaining to the morphology of the interface between gray and white brain matter, or that between brain matter and CSF, or that between CSF and bone. Such information may be used to learn morphological information useful for removing the noise from, and increasing the resolution of, target CT images.

In various embodiments, histological images may be stained to enhance a contrast between different types of tissues. Different stains may be applied to different samples, where the different stains may be selected to facilitate distinguishing between the different types of tissues. For example, a first stain may be applied to a first histological sample, to enhance a contrast between a first tissue and a second tissue; a second stain may be applied to a second histological sample, to enhance a contrast between the first tissue and a third tissue; a third stain may be applied to a third histological sample, to enhance a contrast between the second tissue and the third tissue; and so on. Further, in some embodiments, histological images may be combined, where pixel intensity values of a resulting combined image may be assigned as a function of a first set of pixel intensity values of a first component histological image, a second set of pixel intensity values of a second component histological image, and so on. As with the MR images, relative weightings may be used to combine features of different component histological images. Similarly, a first wavelength, or spectrum of illumination may be applied to a stained or unstained first image.

Referring briefly to FIGS. 7A and 7B, examples of stained histological images are shown. FIG. 7A shows a first stained histological image 700, where a first, silver stain is applied to a first slice of a brain of a subject. As a result of staining first stained histological image 700 with the first silver stain, a first type of tissue 702 of first stained histological image 700 may be easily distinguished from a second type of tissue 704. In contrast, FIG. 7B shows a second stained histological image 750, where a second, parvalbumin stain is applied to a second slice of a brain of a subject. As a result of staining second stained histological image 750 with the second parvalbumin stain, a third type of tissue 752 of second stained histological image 750 may be easily distinguished from a fourth type of tissue 754. Either of third type of tissue 752 and fourth type of tissue 754 may be the same as either of first type of tissue 702 and second type of tissue 704. Thus, by staining and scanning different histological sample slices with different stains, reference images with different desired resolutions and/or contrast and/or CNRs in different portions of the images may be obtained.

Returning to FIG. 4, at 412, method 400 includes generating a plurality of spectral CT images optimized for generating synthetic CT images. Spectral CT images of a scanned subject may be generated by a photon-counting CT (PCCT) imaging device, where radiation detectors of the PCCT device are photon-counting detectors that are capable of differentiating x-ray photons of different energies. The x-ray photons of different energies may be counted and allocated to different bins to provide spectral information. PCCT uses a direct-conversion detector, which has various advantages over conventional indirect-conversion-detector-based Energy Integrating Detector (EID) CT systems and typically produces images with a higher resolution and/or higher CNR than images generated using an EID CT imaging device.

In some embodiments, spectral images are obtained by irradiation using two or more different spectra. In other embodiments, spectrally-sensitive detectors, such as PCCT or multilayer detectors may provide spectral information from a exposure to a single spectrum. Spectral information may, for example, provide larger differentiation between gray and white brain matter than available using a non-spectral scan. The morphological and contrast information provided by the spectral image may provide information useful to remove noise from, and increase the resolution of, a target CT image.

At 414, method 400 includes creating a reference image dataset with spectral, stained histological, and MR images that have been optimized for generating synthetic CT images. The reference image dataset may be a non-limiting example of reference image dataset 254 of FIG. 2B. In some embodiments, the different types of reference images (e.g., MR images, histological images, spectral CT images, and/or other types of images) may be organized in the reference image dataset, or organized by a synthetic CT image generator such as synthetic CT image generator 252, to ensure that synthetic CT images used for training the noise reduction neural network exhibit desired characteristics.

For example, it may be desired that the synthetic images be created from a desired proportion of the different types of reference images. For example, it may be desired that synthetic CT images used for training include a first number of synthetic CT images generated from MR images; a second number of synthetic CT images generated from histological images; a third number of synthetic CT images generated from spectral CT images; and so on, where the first number, second number, and third number may be the same number or different numbers. For example, it may be determined during training of the noise reduction neural network, that synthetic CT images created from a first type of reference image are preferred over a second type of reference image (e.g., where a first performance of a first noise reduction neural network trained on the synthetic CT images created from a first type of reference image is greater than a second performance of a second noise reduction neural network trained on the synthetic CT images created from a second type of reference image).

Figure 5:
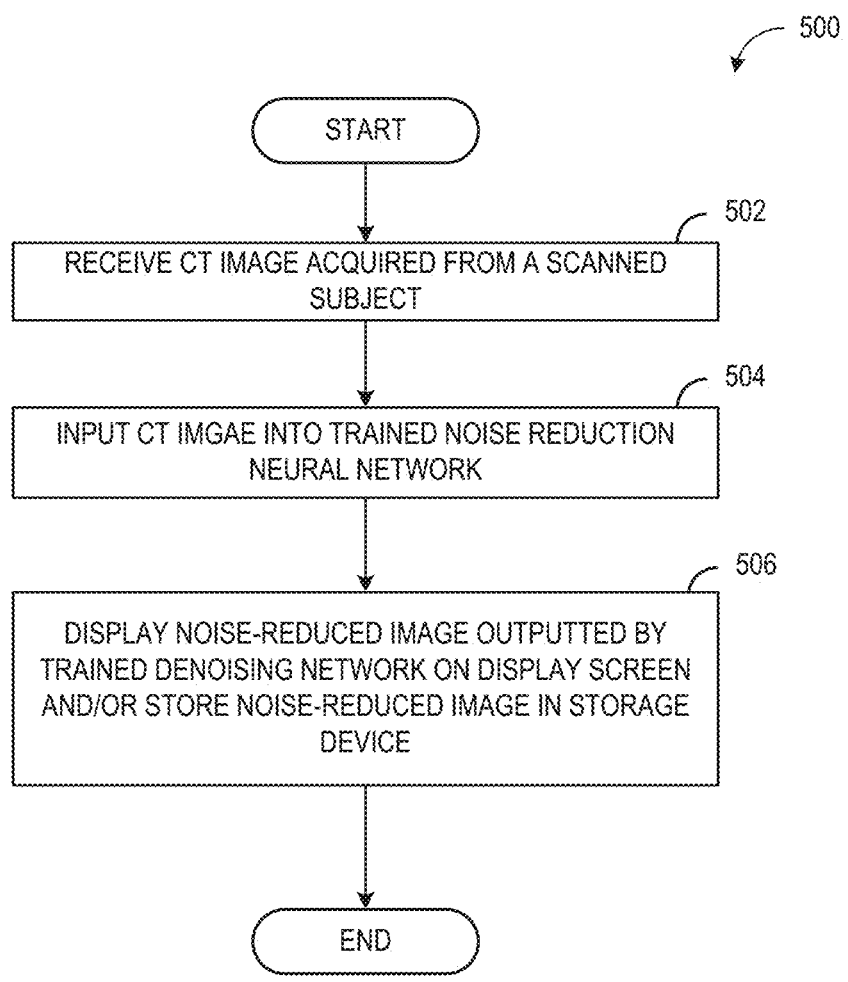
FIG. 5 shows a flowchart illustrating an exemplary method for removing noise from CT images using a trained noise reduction neural network, in accordance with one or more embodiments of the present disclosure.

Referring now to FIG. 5, a flowchart is shown of a method 500 for deploying a noise reduction neural network, such as noise reduction neural network 202 of FIG. 2A, to reduce noise in real CT images. Method 500 may be executed by a processor of an image processing system, such as the image processing system 102 of FIG. 1. Some operations of method 500 may be stored in a non-transitory memory of the image processing system (e.g., in inference module 112 of the image processing system 102 of FIG. 1) and executed by a processor of the image processing system (e.g., the processor 104 of image processing system 102 of FIG. 1). In various embodiments, the noise reduction neural network may be trained as described above in reference to method 300 of FIG. 3, on synthetic training data generated as described above in reference to method 400 of FIG. 4. Specifically, the training data may include one or more sets of image pairs comprising synthetic CT images with different amounts of added noise.

Method 500 begins at 502, where method 500 includes receiving a CT image acquired from a subject. For example, the CT image may be acquired using a CT imaging device such as CT imaging device 230 of FIG. 2A, or CT scanner 136 of the image processing system 102. The acquired CT image may be of a same ROI, and/or may include a same set of anatomical structures as the set of reference images and 2D synthetic images on which the noise reduction neural network is trained. In some embodiments, the subject of the acquired CT image may be similar to subjects of the set of reference images. For example, the subject may be a child, where the acquired CT image may be inputted into a first noise reduction neural network trained on reference images of children; the subject may be female, where the acquired CT image may be inputted into a second noise reduction neural network trained on reference images of women; the subject may be male, where the acquired CT image may be inputted into a third noise reduction neural network trained on reference images of men; and so on.

At 504, the acquired CT image is inputted into the trained noise reduction neural network. In various embodiments, inputting the acquired CT image into the trained noise reduction neural network comprises inputting image data of each pixel of the acquired CT image into a corresponding node of an input layer of the noise reduction neural network. Values of the image data may be multiplied by weights at the corresponding nodes, and propagated through various hidden layers (e.g., convolutional layers) to an output layer of the noise reduction neural network. The output layer may include nodes corresponding to each pixel of an output CT image, where the output CT image is based on image data outputted by each node. The output image may have less noise than the input image, where an amount of the noise of the input image is reduced or removed by the trained noise reduction neural network.

At 506, method 500 includes displaying the noise-reduced image outputted by the trained noise reduction neural network on a display screen of the image processing system (e.g., display device 134 of FIG. 1). The noise-reduced image may be displayed on the display screen in real time during an examination of the subject, such that an operator of the image processing system (e.g., a caregiver) may review the noise-reduced image during the examination. For example, the noise-reduced image may be used to diagnose a condition of the subject. By reducing the amount of noise in the acquired CT image, anatomical features of the subject may be more clearly visible to the caregiver, whereby the condition may be more easily diagnosed.

Figures 8A, 8B, 8C:
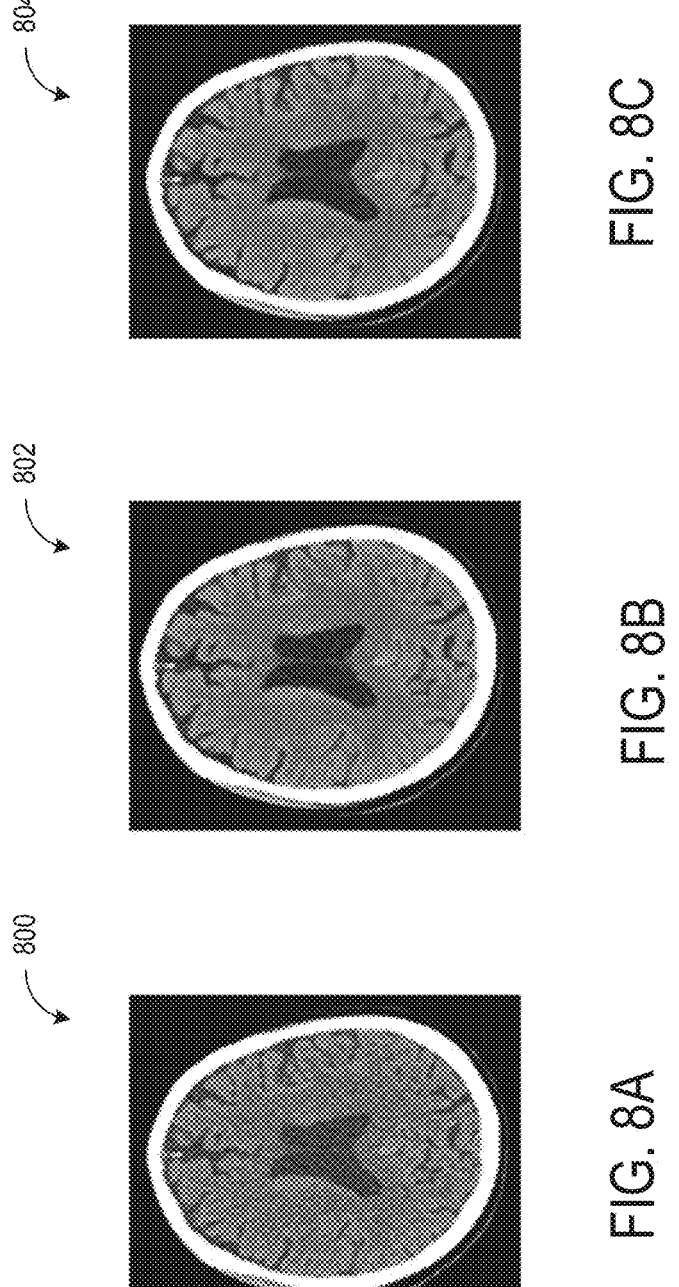
FIG. 8A shows an example CT image inputted into a trained noise reduction neural network, in accordance with one or more embodiments of the present disclosure.
FIG. 8B shows a first example noise-reduced image generated from the example CT image of FIG. 8A by a first noise reduction neural network trained on synthetic CT images, in accordance with one or more embodiments of the present disclosure.
FIG. 8C shows a second example noise-reduced image generated from the example CT image of FIG. 8A by a second noise reduction neural network trained on real CT images, in accordance with one or more embodiments of the present disclosure.
Figure 9:
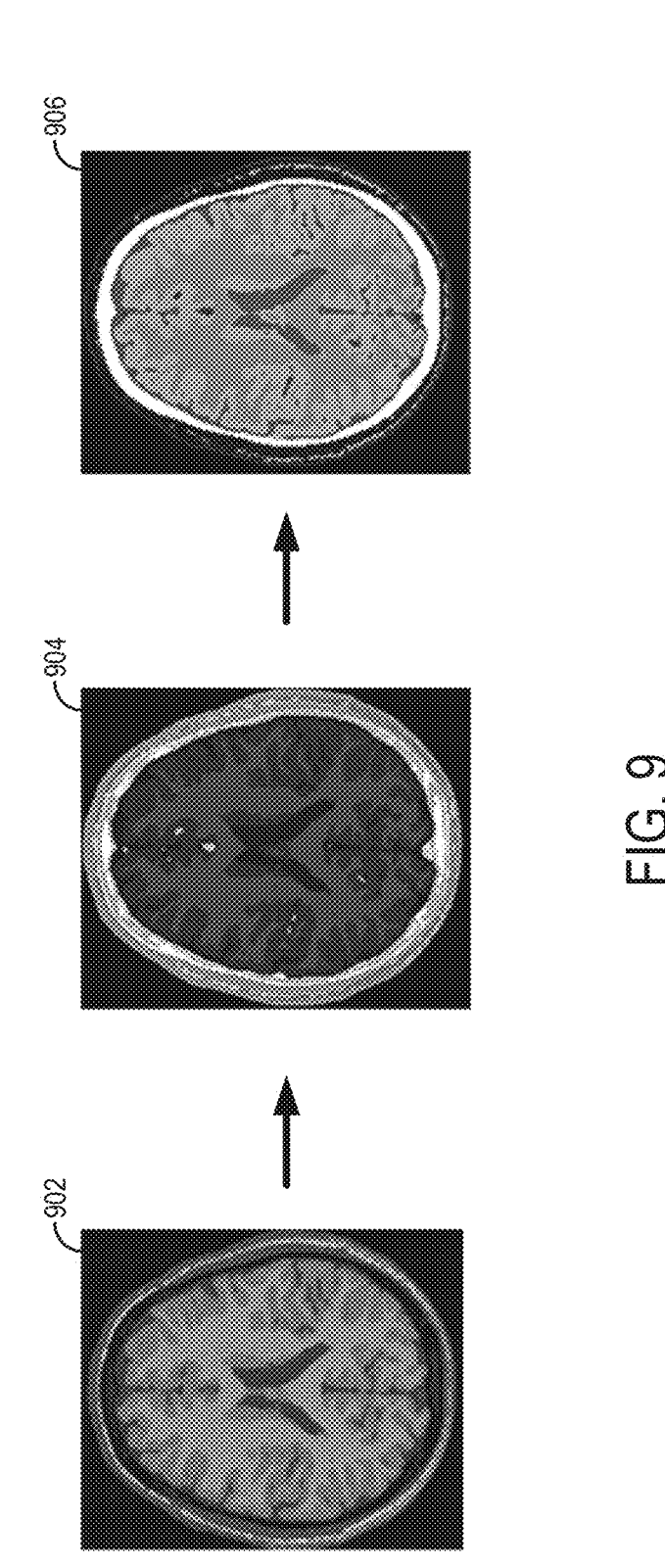
FIG. 9 shows a synthetic CT image created based on a real CT image, in accordance with one or more embodiments of the present disclosure.

FIGS. 8A, 8B, and 8C show examples of input/output pairs of images generated using trained noise reduction neural networks such as the noise reduction neural network described herein. FIG. 8A shows an input image 800, where input image 800 is a CT image acquired from a subject during an examination. Specifically, input image 800 is a CT image of a brain of the subject, which includes noise. FIG. 8B shows a first output image 802. First output image 802 is outputted by a first trained noise reduction neural network based on input image 800 (e.g., where input image 800 is inputted into the first trained noise reduction neural network to generate output image 802). The first noise reduction neural network is trained using synthetic CT images, such as the synthetic CT images described in relation to FIGS. 2A and 2B and generated as described in method 400 of FIG. 4. In other words, the first noise reduction neural network is trained on image pairs including target CT images with low amounts of noise (e.g., synthetic CT images 212), and noisy synthetic CT input images where noise is added to the target CT images (e.g., noisy synthetic CT images 216).

In contrast, FIG. 8C shows a second output image 804, where second output image 804 is outputted by a second trained noise reduction neural network based on input image 800 (e.g., where input image 800 is inputted into the second trained noise reduction neural network to generate output image 804). The second noise reduction neural network is trained on real CT image pairs, and not on synthetic CT images. In other words, the second noise reduction neural network is trained on image pairs including target CT images acquired from subjects with low amounts of noise (e.g., by performing a high-dose CT scan), and noisy real CT input images where noise is added to the target CT images. As can be seen by comparing FIG. 8B to FIG. 8C, the noise-reduced image 802 of FIG. 8B has a higher resolution and CNR than the noise-reduced image 804 of FIG. 8C. Thus, a first performance of the first noise reduction neural network trained on the synthetic CT image data may be higher than a second performance of the second noise reduction neural network trained on the real CT image data, where more noise is removed by first noise reduction neural network than by second noise reduction neural network.

Thus, systems and methods are described herein for increasing a performance of a noise-reducing or denoising neural network, by training the neural network on synthetic CT images rather than real CT images. By using the synthetic CT images rather than the real CT images, the neural network may more easily learn to distinguish noise from anatomical features in an image. Unlike other approaches to generating synthetic CT images based on using machine learning models, the synthetic CT images described herein may be created based on a tissue segmentation process that may be manual, automated or partially manual and partially automated, and that does not rely on a fully trained prediction model. Further, the synthetic CT images may be generated from reference images that have a higher resolution or CNR than CT images, thereby increasing a quality of the synthetic CT images. The reference images may be MR images, histological images, spectral CT images, PET images, SPECT images, or other types of high-resolution images. These images may be obtained from one or more different animal species. A further advantage of the systems and methods described herein is that the synthetic CT images may be generated from MR reference images acquired with different pulse sequences, which may be combined to create MR reference images that are optimized for synthetic CT image creation. Because the MR reference images acquired with the different pulse sequences may be acquired during an acquisition of each slice of a full image volume, the use of an atlas or registration to ensure an anatomical alignment between component MR images may not be relied on. Fusion (generally deformable registration) of images, where the component images are affected by motion/changes which occurs between acquisitions of the component images, potentially introduces errors. Such errors are particularly undesirable when the object is to capture the morphology and contrast information so that this can be used to denoise and/or increase the resolution of a target image. By reducing the delay between the imaging acquisitions of the same region in successive images, the deleterious effect of motion/changes may be reduced.

The technical effect of creating synthetic CT images from high-resolution reference images such as MR images, and training a noise reduction neural network on the synthetic CT images rather than real CT images, is that a performance of a trained noise reduction neural network in reducing noise in CT images may be increased.

The disclosure also provides support for a method for creating synthetic computed tomography (CT) images for training a neural network model to reduce an amount of noise in acquired CT images, the method comprising: performing a tissue segmentation of reference images of an anatomical region of a subject to determine a set of different tissue types of the reference images, and generating synthetic CT images of the reference images by assigning CT image values of the synthetic CT images based on the different tissue types. In a first example of the method, the reference images have a higher resolution than the acquired CT images. In a second example of the method, optionally including the first example, the method further comprises: performing a scan of the anatomical region to generate a reference image, using one of: magnetic resonance (MR) imaging, CT imaging, multi-energy CT imaging, spectral CT imaging, and positron emission tomography (PET) imaging. In a third example of the method, optionally including one or both of the first and second examples, the scan is a multi-sequence MR scan, and the reference image is a composite image created from a plurality of MR images, each image of the plurality of MR images generated using a different type of pulse sequence, the different types of pulse sequences applied during each slice of the multi-sequence MR scan. In a fourth example of the method, optionally including one or more or each of the first through third examples, the method further comprises: modifying one or more technical parameters of a pulse sequence of the different types of pulse sequences to increase a resolution of a synthetic CT image, the one or more technical parameters including: a slice thickness defined by the pulse sequence, an effective pulse echo sequence weighted by spin-lattice nuclear relaxation; an effective pulse echo sequence weighted by spin-spin nuclear relaxation; an effective pulse echo sequence weighted based on a decay of transverse magnetization caused by a combination of spin-spin relaxation and magnetic field inhomogeneity; a proton-density weighting defined by the pulse sequence; a fat nulling defined by the pulse sequence, and a diffusion weighting defined by the pulse sequence. In a fifth example of the method, optionally including one or more or each of the first through fourth examples, the reference images include a histological image generated from a stained slice of the anatomical region. In a sixth example of the method, optionally including one or more or each of the first through fifth examples, the method further comprises: manually performing the segmentation. In a seventh example of the method, optionally including one or more or each of the first through sixth examples, the method further comprises: performing the segmentation using one or more statistical techniques, the one or more statistical techniques including thresholding and k-means clustering. In an eighth example of the method, optionally including one or more or each of the first through seventh examples, the method further comprises: performing the segmentation using a neural network. In a ninth example of the method, optionally including one or more or each of the first through eighth examples, the method further comprises: using a realistic noise model to add an amount of noise to a first synthetic CT image of the synthetic CT images, to generate a second, noisy synthetic CT image, creating a training image pair including the second, noisy synthetic CT image as an input image and the first synthetic CT image as a ground truth image, training the neural network model on training data including the training image pair. In a tenth example of the method, optionally including one or more or each of the first through ninth examples, the realistic noise model is based on one of image-based noise insertion and projection-based noise insertion. In an eleventh example of the method, optionally including one or more or each of the first through tenth examples, the noise is added in accordance with a Gaussian distribution.

The disclosure also provides support for an image processing system comprising: a processor communicably coupled to a non-transitory memory storing a neural network, the memory including instructions that when executed cause the processor to: receive a plurality of synthetic computed tomography (CT) images, each synthetic CT image generated by performing a tissue segmentation of a magnetic resonance (MR) scan of a subject and assigning CT image values to types of tissues identified by the tissue segmentation, for each synthetic CT image of the plurality of synthetic CT images, add noise to the synthetic CT image to create a noisy version of the synthetic CT image, create a respective plurality of image pairs, each image pair including a synthetic CT image as a target, ground truth image, and a corresponding noisy version of the synthetic CT image as an input image, train the neural network using the image pairs, deploy the trained neural network to generate noise-reduced images from CT images acquired from a scanned subject, and display the noise-reduced images on a display device of the image processing system. In a first example of the system, the MR scan is a multi-sequence MR scan, and the synthetic CT image is generated from a combination of a plurality of MR images acquired from a same slice of the MR scan, each MR image of the plurality of MR images generated using a different pulse sequence. In a second example of the system, optionally including the first example, further instructions are included in the non-transitory memory that when executed, cause the processor to perform the tissue segmentation using a neural network. In a third example of the system, optionally including one or both of the first and second examples, the noise is added using either image-based noise insertion or projection-based noise insertion.

The disclosure also provides support for a method for an image processing system, comprising: acquiring a reference image of an anatomical region of a subject, segmenting tissues of the reference image, assigning voxel intensity values to different tissue types of the reference image to generate a first synthetic computed tomography (CT) image corresponding to the reference image, adding noise to the first synthetic CT image to generate a second, noisy synthetic CT image, creating a training image pair including the second synthetic CT image as an input image, and the first synthetic CT image as a ground truth image, training a convolutional neural network (CNN) to remove noise from synthetic CT images, using training data including the training image pair, using the trained CNN to remove noise from a real CT image acquired from a scanned subject, and displaying a noise-reduced version of the real CT image on a display device of the image processing system and/or storing the noise-reduced version in a memory of the image processing system. In a first example of the method, segmenting the tissues of the reference image further comprises manually segmenting the tissues of the reference image. In a second example of the method, optionally including the first example, the method further comprises: acquiring the reference image from one of an MR scan, a CT spectral imaging scan, or a histology sample. In a third example of the method, optionally including one or both of the first and second examples, the reference image is a multi-sequence MR scan, and the reference image is created by combining a plurality of MR images acquired during a single slice of the MR scan, each MR image of the plurality of MR images generated by a different pulse sequence.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. An image processing system comprising:
   a processor communicably coupled to a non-transitory memory storing a neural network, the memory including instructions that when executed cause the processor to:
      receive a plurality of synthetic computed tomography (CT) images, each synthetic CT image generated by performing a tissue segmentation of a reference image of a plurality of reference images of a subject and assigning CT image values to types of tissues identified by the tissue segmentation;
      for each synthetic CT image of the plurality of synthetic CT images, add noise to the synthetic CT image to create a noisy version of the synthetic CT image;
      create a respective plurality of image pairs, each image pair including a synthetic CT image as a target, ground truth image, and a corresponding noisy version of the synthetic CT image as an input image;
      train the neural network using the image pairs;
      deploy the trained neural network to generate noise-reduced images from CT images acquired from a scanned subject; and
      display the noise-reduced images on a display device of the image processing system;
      wherein the plurality of reference images include a composite image generated from a combination of a plurality of magnetic resonance (MR) images, each MR image of the plurality of MR images acquired from a same slice of a scan of a patient using a different pulse sequence.

2. The image processing system of claim 1, wherein further instructions are stored in the memory that when executed, cause the processor to:
   select, from the plurality of MR images acquired from the same slice, a set of MR images having a resolution greater than a threshold resolution; and
   generate the composite image from the set of MR images.

3. The image processing system of claim 1, wherein the plurality of reference images includes histological images taken from anatomical samples.

4. The image processing system of claim 1, wherein the noise is added using projection-based noise insertion.

5. A method for an image processing system, comprising:
   acquiring a reference image of an anatomical region of a subject;
   segmenting tissues of the reference image;
   assigning voxel intensity values to different tissue types of the reference image to generate a first synthetic computed tomography (CT) image corresponding to the reference image;
   adding noise to the first synthetic CT image to generate a second, noisy synthetic CT image;
   creating a training image pair including the second synthetic CT image as an input image, and the first synthetic CT image as a ground truth image;
   training a convolutional neural network (CNN) to remove noise from synthetic CT images, using training data including the training image pair;

using the trained CNN to remove noise from a real CT image acquired from a scanned subject; and displaying a noise-reduced version of the real CT image on a display device of the image processing system and/or storing the noise-reduced version in a memory of the image processing system;

wherein the reference image is a composite image generated from a combination of a plurality of magnetic resonance (MR) images, each MR image of the plurality of MR images acquired from a same slice of a scan of a patient using a different pulse sequence.

6. The method of claim 5, wherein segmenting the tissues of the reference image further comprises manually segmenting the tissues of the reference image.

7. The method of claim 5, wherein the reference image is one of a plurality of reference images used to create training data for training the CNN, and the plurality of reference images further includes images acquired from a CT spectral imaging scan, a positron emission tomography (PET) scan, and a CT spectral imaging scan.

8. The method of claim 7, wherein the plurality of reference images further includes images acquired from histology samples.

9. The image processing system of claim 3, wherein the histological images include a first histological image obtained with a first stain, and a second histological image obtained with a second stain.

10. The image processing system of claim 3, wherein the histological images include a first histological image obtained with a first illumination spectrum, and a second histological image obtained with a second illumination spectrum.

11. The image processing system of claim 1, wherein the plurality of reference images includes positron emission tomography (PET) images.

12. The image processing system of claim 11, wherein the PET images include a first PET image obtained with a first tracer agent, and a second PET image obtained with a second tracer agent.

13. The image processing system of claim 1, wherein the plurality of reference images includes spectral CT images.

14. The image processing system of claim 1, wherein the plurality of reference images includes single photon emission computerized tomography (SPECT) images.

* * * * *